United States Patent [19]
Guttman et al.

[11] Patent Number: 5,964,999
[45] Date of Patent: Oct. 12, 1999

[54] METHODS FOR PROFILING OLIGOSACCHARIDES RELEASED FROM GLYCOPROTEINS

[75] Inventors: Andras Guttman, Fullerton; Nelson H. Cooke, Anaheim Hills, both of Calif.

[73] Assignee: Beckman Instruments, Inc., Fullerton, Calif.

[21] Appl. No.: 08/768,515

[22] Filed: Dec. 18, 1996

Related U.S. Application Data

[62] Division of application No. 08/589,042, Jan. 19, 1996, Pat. No. 5,662,787.

[51] Int. Cl.$^6$ .......................... G01N 27/26; G01N 27/447
[52] U.S. Cl. .......................... 204/455; 204/468; 204/469; 204/606
[58] Field of Search ..................................... 204/451, 452, 204/453, 454, 455, 601, 602, 603, 604, 605, 469, 468

[56] References Cited

PUBLICATIONS

A. Pervin et al, "Separation of Glycosaminoglycan–Derived Oligosaccharides by Capillary Electrophoresis Using Reverse Polarity" Analytical Biochemistry 221 No month available (1994) 182–188.

Fu–Tai A. Chen et al, "Analysis of Mono– and Oligosaccharide Isomers Derivatized with 9–Aminopyrene–1,4, 6–trisulfonate by Capillary Electrophoresis with Laser–Induced Fluorescence" Analytical Biochemistry 230 No month available (1995) 273–280.

Wassin Nashabeh et al, "Capillary zone electrophoresis of linear and branched oligosaccharides" Journal of Chromatography 600 No month available (1992) 279–287.

András Guttman et al "Capillary electrophoresis separation of oligosaccharides: I. Effect of operational variables" Electrophoresis No month available 1994, 15 1–5.

Wassim Nashabeh et al "Capillary zone electrophoresis of α–acid glycoprotein fragments from trypsin and endoglycosidase digestions" Journal of Chromatography 550 No month available (1991) 31–42.

Myriam Taverna et al "Analysis of carbohydrate–mediated heterogeneity and characterization N–linked oligosaccharides of glycoproteins by performance capillery electrophoresis" Electrophoresis No month available (1992) 359–366.

Wassim Nashabeh et al "Capillary zone electrophoresis of pyridylamino derivatives of maltooligosaccharides" Journal of Chromatography 514 No month available (1990) 57–64.

Yehia Mechref et al "Capillary zone electrophoresis of derivatized acid monosaccharides" Electrophoresis 15 No month available (1994) 627–634.

Hiroshi Kitagawa et al, "Microanalysis of Glycosaminoglycan–Derived Disaccharides Labelled with the Fluorophore 2–Aminoacridone by Capillary Electrophoresis and High–Performance Liquid Chromatography" Analytical Biochemistry 232 No month available (1995) 114–121.

*Primary Examiner*—William H. Beisner
*Assistant Examiner*—John S. Starsiak, Jr.
*Attorney, Agent, or Firm*—William H. May; P. R. Harder; Margaret A. Kivinski

[57] ABSTRACT

Methods for profiling oligosaccharides released from glycoproteins and methods for the electrophoretic separation of high mannose, complex and hybrid oligosaccharides are disclosed. The methods include first providing an analytical sample which includes at least one released oligosaccharide and introducing the sample into an electrophoretic channel containing a separation medium having a pH less than 8 and greater than 2.5. Then applying a sufficiently high electric field causes the released oligosaccharides to migrate and separate within the electrophoretic channel in accordance with their molecular size or charge to mass ratio. Detecting the separated oligosaccharides provides glycoprotein conjugate profiling information. Preferred embodiments include using a separation medium which includes lithium acetate buffer having a pH of about 4.75 and a gel of about 0.4% polyethylene oxide.

16 Claims, 10 Drawing Sheets

Asialo triantennary (FT 02)

Gal(β1,4)GlcNAc(β1,2)Man(α1,6)
　　　　　　　　　　　　｜
　　　　　　　　　　　　　　　Man(β1,4)GlcNAc(β1,4)GlcNAc
　　　　　　　　　　　　　　　｜
Gal(β1,4)GlcNAc(β1,2)Man(α1,3)
　　　　　　｜
Gal(β1,4)GlcNAc(β1,4)

Sialylated triantennary (2 x α2,6) (FT 07):

NeuAc(α2,6)Gal(β1,4)GlcNAc(β1,2)Man(α1,6)
　　　　　　　　　　　　　　　　　　　｜
　　　　　　　　　　　　　　　　　　　　　　Man(β1,4)GlcNAc(β1,4)GlcNAc
　　　　　　　　　　　　　　　　　　　　　　｜
NeuAc(α2,6)Gal(β1,4)GlcNAc(β1,2)Man(α1,3)
　　　　　　　　　　　｜
NeuAc(α2,3)Gal(β1,4)GlcNAc(β1,4)

Sialylated triantennary (2 x α2,3) (FT 07A):

NeuAc(α2,3)Gal(β1,4)GlcNAc(β1,2)Man(α1,6)
　　　　　　　　　　　　　　　　　　　｜
　　　　　　　　　　　　　　　　　　　　　　Man(β1,4)GlcNAc(β1,4)GlcNAc
　　　　　　　　　　　　　　　　　　　　　　｜
NeuAc(α2,6)Gal(β1,4)GlcNAc(β1,2)Man(α1,3)
　　　　　　　　　　　｜
NeuAc(α2,3)Gal(β1,4)GlcNAc(β1,4)

METHODS FOR PROFILING OLIGOSACCHARIDES RELEASED FROM GLYCOPROTEINS

This application is a Divisional Application of U.S. application Ser. No. 08/589,042 filed Jan. 19, 1996, now U.S. Pat. No. 5,662,787.

BACKGROUND OF THE INVENTION

1. Field of the Invention

The present invention relates generally to methods for the electrophoretic separation and analysis of oligosaccharides. More particularly, the present invention relates to analytical methods involving electrophoretic based profiling of oligosaccharides following their chemical or enzymatic release from glycoproteins.

2. Description of Relevant Art

Complex carbohydrates are important components of all living things. In addition to providing energy and structural supports for cells, increasing evidence has shown that the carbohydrate moieties of glycoconjugates are often important as recognition determinants in receptor-ligand or cell-cell interactions, in the modulation of immunogenicity and protein folding, and in the regulation of protein bioactivity. Changes in the biological activity of glycoproteins often result from alterations in protein glycosylation either through variable site occupancy or changes in the structure of the oligosaccharide occupying a particular site.

For these reasons biochemists have increasingly recognized the benefits associated with the ability to obtain molar ratios or patterns of oligosaccharide structures of glycoproteins. It is equally desirable to have the ability to determine the degree of glycosylation and to detect changes in the extent of and the nature of the glycosylation of proteins.

Recently there have been rapid developments in methodologies for analyzing oligosaccharide structures of native and recombinant glycoproteins. Anion exchange chromatography, reverse phase high pressure liquid chromatography, mass spectrometry, nuclear magnetic resonance spectroscopy and more recently electrophoretic methods have all been investigated for their usefulness in profiling the oligosaccharide structures of glycoproteins with varying degrees of success. The most common methods for profiling asparagine linked (N-linked) oligosaccharides involve releasing the oligosaccharides with peptide-N-glycosidase F(PNGase F) and profiling the released oligosaccharides by high pH anion exchange chromatography or slab gel electrophoretic separations.

Profiling information obtained from high pH anion exchange chromatography depends upon the ionic strength of the released oligosaccharides, and, because some molecular sieving takes place, it also depends upon the effective or apparent molecular weight of the oligosaccharides. While effective molecular weight is a measure of molecular size, effective molecular weight primarily depends upon the oligosaccharide hydrodynamic volume. Hydrodynamic volume is determined by the oligosaccharide molecular weight and the degree to which the oligosaccharide is hydrated by the medium in which the oligosaccharide is being analyzed. Thus, different oligosaccharides which have been analyzed by high pH anion exchange chromatography may have the same molecular weight or molecular size but will appear to have different molecular size because the degree to which they are hydrated is different. Reliable molecular size correlation data which takes into account the relative amount of hydration experienced by different saccharides, is available. However, this data depends upon a qualitative knowledge of the oligosaccharide being investigated. Also, oligosaccharides released from glycoproteins frequently contain one or more sialic acid residues which can alter dramatically the charge and the hydrodynamic volume of the oligosaccharide. In these cases, high pH anion exchange chromatography provides little reliable molecular size information. Thus, to obtain reliable relative oligosaccharide molecular weight information from high pH anion exchange chromatography data it is preferable to know the degree to which the glycoprotein is sialylated.

Electrophoretic based separations for profiling oligosaccharides represent an improvement over high pH anion exchange chromatography because electrokinetic migration of any given compound is primarily dependent upon only its mass to charge ratio. Typically, these electrophoretic methods utilize high pH (greater than 8.3) borate buffer electrophoretic mediums. The borate complexes with the oligosaccharide hydroxyl moieties providing the charge required for electrokinetic movement. One disadvantage associated with these borate buffer systems is the electrophoretic migration pattern of the borate complexed oligosaccharides. These complexes will migrate in a reverse direction (i.e. large structure migrate first) rendering the identification of the structures imprecise and difficult. Typically, in order to achieve low detection limits with very small sample volumes characteristic of capillary electrophoretic separations, saccharides are pre-labeled with a fluorescent labeling compound at the saccharide reducing end. When the label is charged, the oligosaccharides have the same charge and will electrokinetically migrate according to their mass to charge ratio When the oligosaccharides are not sialylated, all of the structures possess the same charge and the resulting data provides relative size information about the separated and detected saccharides.

This approach presents problems when analyzing oligosaccharide structures of sialylated glycoproteins. Sialic acid becomes negatively charged at pHs of about 7 to 8. Under electrophoresis conditions which utilize running buffers having a pH above 8, the sialic acid component of the released oligosaccharide is ionized. In this case, in addition to the problems discussed above, each oligosaccharide may have different charge distributions, so the electrokinetic migration order of the sialylated compounds effects the mass to charge ratio. To obtain relative size information for such oligosaccharides, the cleaved compounds must be desialylated and then electrophoresed. In this manner the relative sizes of the desialylated oligosaccharides are known but information relating to the relative size of sialylated residues is not determined directly.

In cases involving glycoprotein conjugate profiling under conditions in which the electrophoresis conditions include a low pH buffer of about 2.5, the sialylated oligosaccharides tend to co-migrate resulting in very poor separations.

It is an object of the present invention to provide methods for profiling glycoprotein linked high mannose, complex and hybrid oligosaccharides. It is also an object of the present invention to provide methods for obtaining molar ratios and relative molecular weights of individual oligosaccharides. It is further an object of the present invention to provide methods for detecting changes in the extent or nature of glycosylation, including changes in the extent of sialylation.

SUMMARY OF THE INVENTION

The present invention accomplishes these and other objectives by providing electrophoresis methods for separating high mannose, complex, and hybrid oligosaccharides under conditions which assure that all oligosaccharides have the same effective charge. This assures that the migration order of each separated oligosaccharide depends upon the molecular weight of the oligosaccharide. The methods of the present invention are particularly useful in combination with analytical techniques which involve the release of oligosaccharides from glycoproteins and the subsequent analysis of the released oligosaccharides. The methods of the present invention are also suitable for use in glycoprotein/glycopeptide sequencing applications in which knowledge relating to the nature or profile of the glycoconjugates is desirable.

In particular, the present invention relates to profiling oligosaccharides released from glycoproteins, and involves first providing an analytical sample which includes at least one released oligosaccharide and then introducing the sample of released oligosaccharides into an electrophoresis channel containing an electrophoretic separation medium of having a pH less than 8 and greater than 2.5. Next, applying a sufficient electric field to the electrophoresis channel causes the released oligosaccharides to electrophoretically migrate within the electrophoresis channel in accordance with their molecular size or charge to mass ratio. The final step involves detecting the separated oligosaccharides in order to obtain glycoprotein conjugate profiling information.

The methods described herein are most useful when the released oligosaccharides have sialic acid residues incorporated in their structure. However, those skilled in the art will recognize that the methods of the present invention are also suitable for separating released oligosaccharides having no sialic acid residues.

In preferred embodiments the present invention involves enzymatically cleaving asparagine (N) linked or methionin/threonine (O) linked oligosaccharides from glycoproteins and labeling the cleaved oligosaccharides at their reducing end with a fluorescent label. The preferred method further includes subjecting the labeled oligosaccharides to capillary electrophoresis using an electrophoresis separation medium which includes a lithium acetate buffer having a pH of about 4.75 and a gel of about 0.4 wt % polyethylene oxide. In order to keep unwanted electroosmotic flow to a minimum and maintain good analytical reproducibility, it is preferable to utilize a capillary having an interior wall coating. Preferred coated capillaries are those having a combination of polyolefin and polyvinylalcohol available from Beckman Instruments under the Tradename e-CAP™. Advantageously, detecting the oligosaccharides is accomplished using a fluorescent detector to detect the fluorescent label. Those skilled in the art will recognize that the combination of fluorescent label and fluorescent detection provides enhanced detection capabilities.

These and other features associated with the present invention will become apparent to those skilled in the art upon an understanding of the invention as described below when viewed in combination with the following drawings.

DETAILED DESCRIPTION OF THE INVENTION

The present invention provides improved methods for profiling oligosaccharide having been released from glycoproteins. Unlike prior art oligosaccharide conjugate separation methods, which can result in ambiguous molecular size and distribution information; can fail to separate sialylated conjugates and require cumbersome and inefficient separation times, the methods of the present invention provide rapid and accurate molecular size information for both sialylated and nonsialylated or desialylated oligosaccharide glycoprotein conjugates. The methods of the present invention can also be utilized to identify glycoprotein glycan conjugates.

The methods of the present invention incorporate procedures for releasing oligosaccharides from the glycoprotein conjugates. Although, the methods for cleaving oligosaccharides described herein involve enzymatic cleaving methods, those skilled in the art will recognize that such procedures can be carried out using standard enzymatic and chemical cleavage methods suitable for cleaving and releasing glycoproteins conjugates. Similarly, the electrophoretic separation conditions described herein can be carried out using any electrophoresis system. Particularly suitable systems include the P/ACE electrophoresis system sold by Beckman Instruments of Fullerton, Calif. Additionally, as described in more detail below, standard carbohydrate labeling methods known by those skilled in the art are applicable for enabling the detection of separated oligosaccharides and incorporating a charged moiety to the oligosaccharide.

The present invention is based upon the discovery that by using an electrophoretic separation medium which includes a buffer having a pH less than about 8 and greater than about 2.5, oligosaccharides which have been cleaved from their glycoprotein conjugates can be electrophoretically separated to obtain reliable quantitative oligosaccharide profiling information. More particularly, the present invention includes oligosaccharide analysis processes which involve first providing an analytical sample of released oligosaccharides and then introducing the sample into an electrophoresis channel. The electrophoresis channel includes an electrophoresis separation medium having a pH of less than 8.0 and greater than 2.5. Then applying to the electrophoresis channel an electric field sufficient to cause the released oligosaccharides to electrophoretically and differentially migrate within the electrophoresis separation medium, causes the oligosaccharides to separate within the electrophoresis channel. Detecting the separated oligosaccharide provides information relating to their relative molecular size. Additionally, the detected separated oligosaccharides can provide information relating to changes in glycosylation or sialylation of the glycoprotein. Finally, the electropherograms can provide information relating to the identity of the oligosaccharides based upon comparisons with electropherograms of standard samples and other analytical techniques.

The methods of the present invention can be applied to any glycoprotein and the methods particularly benefit the analysis of glycoproteins in which the oligosaccharide conjugates are sialylated or those in which one or more of the oligosaccharide conjugates contain sialic acid at the non-reducing terminal sugar unit. However, the methods described herein provide reliable and quantitative profiling information irrespective of the presence of sialic acid residues. Preferably, if the glycoprotein is not available or supplied in pure form, prior to cleaving and releasing its oligosaccharide conjugates the glycoprotein is purified in accordance with standard purification procedures. Such procedures typically involve sequential dissolution and precipitation and/or chromatographic purification techniques.

In accordance with the present invention, to obtain released oligosaccharides, purified glycoprotein of interest is chemically or enzymatically treated under conditions which cleave and release the oligosaccharide conjugates. Chemistries for cleaving and releasing asparagine linked oligosaccharide conjugates and chemistries for cleaving and releasing methionin/threonine linked oligosaccharide conjugates, are equally suitable in the practice of the present invention. The choice of procedure depends upon the nature of the conjugate link in the glycoprotein and personal choice. Those skilled in the art recognize that such procedures can be carried out using standard enzymatic and chemical cleavage methods suitable for cleaving and releasing glycoproteins conjugates. A preferred method for cleaving asparagine linked oligosaccharide conjugates involves an enzymatic release using PNGase F as known in the art. Methionin/threonine linked conjugates can be cleaved and released by hydrasinolisis.

Subsequent to treating the glycoprotein to release the oligosaccharide conjugates, preferred embodiments include isolating the cleaved oligosaccharides from the proteins. As known in the art such procedures typically involve a cold ethanol precipitation step with a subsequent filtration or centrifugation step to remove the precipitated protein from the cleaving solution.

To assure that the released oligosaccharides are charged so that they electrokinetically migrate in an applied electric field, and to provide the oligosaccharides with a label for detection purposes, the next step in the present process involves labeling the released oligosaccharides with a detectable charged label. Suitable labels include charged ultra-violet chromophores, visible chromophores, charged moieties having a radioactive label, charged fluorophores, and moieties capable of detection by electrochemical or chemiluminescent detectors. Because fluorophores are widely available, are generally safe to use and offer very good detection limits, especially when used in combination with laser induced fluorescent detectors, preferred embodiments incorporate fluorophore labels. Labeling methodologies, including oligosaccharide labeling chemistries, are well known in the art and typically involve reductive amination of the sugar reducing end or other derivatization methods such as condensation with 1-phenyl-3-methyl-5-pyrazolone. Since reductive amination provides good versatility in the selection of labels and good yields of labeled oligosaccharide, it is the preferred labeling method.

Figure 9:
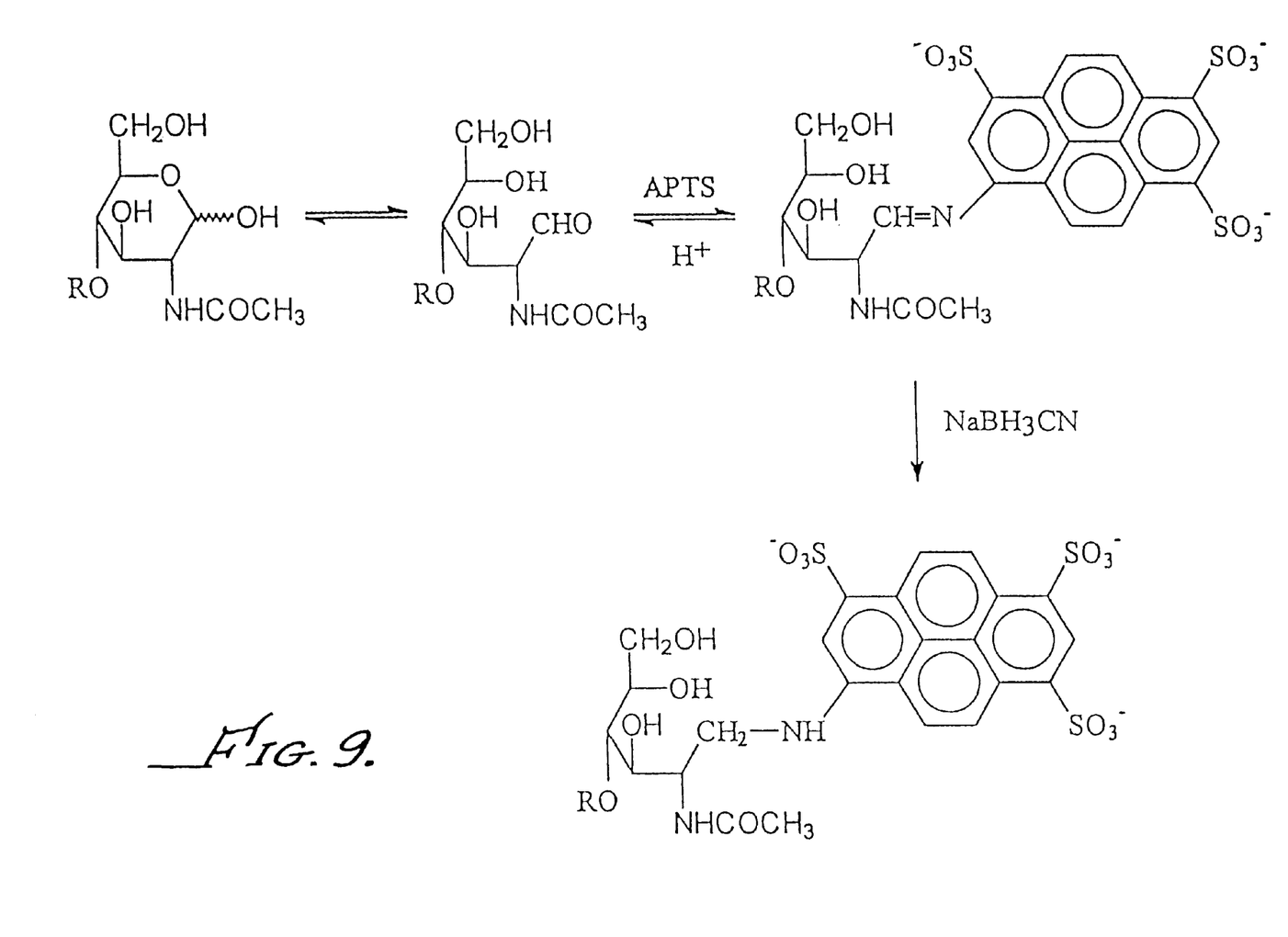
FIG. 9 illustrates the reductive amination reaction between APTS and a sugar moiety.

Reductive amination procedures are known in the art and typically involve reacting the reducing end of the sugar with the amino group of the labeling compound to form a Shiff base. Generally a second sodiumcyanoborohydride reducing step is incorporated in the reaction in order to shift the equilibrium to the labeled compounds. A wide variety of commercially available aminated derivatization reagents are suitable as labeling agents for purposes of the present invention. These include but are not limited to ultra-violet absorbing compounds such as 2-aminopyridine, 6-aminoquinoline, 4-aminobenzoic acid, ethyl 4-aminobenzoate and aminobenzonitrile. Suitable fluorescent labels include 3-(4-carboxybenzoyl)-2-quinolinecarboxaldehyde, tetramethylrhodamine, 8-aminonaphthalene-1,3,6-trisulfonate, and 1-aminopyrene-3,6,8-trisulfonate (APTS). APTS is particularly preferred because excess unreacted APTS in a labeling solution has about 40 times less fluorescence at detection wavelengths compared to the labeled oligosaccharides. Thus, excess unreacted labeling reagent in the solution is less likely to overlap or interfere with the analyte peaks in the resulting electropherograms. Also the excitation and emission characteristics of APTS allows the use of readily available Ar-ion lasers in a laser induced fluorescent detector. These lasers will effectively excite APTS labeled compounds with a 488 nm excitation and the labeled compounds can be subsequently detected at its 520 nm emission. FIG. 9 schematically illustrates a reductive amination reactions between a sugar moiety and APTS.

In accordance with the methods of the present invention the next step includes electrophoretically separating the labeled oligosaccharides in an electrophoretic channel which includes an electrophoretic separation medium having a pH of less than about 8 and more than about 2.5. While preferred electrophoretic separation systems are those in which the separation occurs in a capillary, those skilled in the art will recognize that a variety of separation channels can be utilized including planar capillary electrophoresis systems which are etched in glass surfaces, e.g. silicon wafers.

The capillary electrophoretic separation steps of the present invention can be carried out using any electrophoresis system, a number of which are commercially available. Particularly suitable systems include the P/ACE electrophoresis system sold by Beckman Instruments of Fullerton, Calif. Carrying out the electrophoresis step involves introducing a sample of isolated and labeled oligosaccharide into one end of a buffer containing capillary and applying an electric field to the capillary sufficient to cause electrokinetic migration of the labeled oligosaccharide.

As mentioned above, the pH of the buffer is important for the effective separation of the oligosaccharides. By keeping the pH below 8 the order of migration allows for effective identification of the oligosaccharide structure. Similarly, maintaining the pH above 2.5 provides effective separation of sialic acid containing oligosaccharides. Since in most cases the label is the source of the charge to the oligosaccharides the pH should also be such that the label remains charged. Since many of the labels are strong acids, pH's above about 2.5 are effective in maintaining the charge on the oligosaccharide. Preferred electrophoretic mediums are adjusted to a pH of between 4 and 5 and further include a gel which provides a molecular sieving component to the separation. In effect the sieving component gives the separation improved resolution, sharper peaks, and thus better quantitative data.

In most preferred embodiments of the present invention, the electrophoretic medium includes an acetate buffer and gel adjusted to a pH of about 4.75. The gel is a polyethylene oxide having a molecular weight greater than 100,000 and preferably a molecular weight on the order of 300,000. In order to adjust the pH of the lithium acetate buffer, the electrophoretic medium is treated with phosphoric acid. It is believed that using a lithium acetate buffer in the electrophoretic separation medium results in a significantly reduced current during the electrophoretic process. These reduced current separations are characterized as having a significantly reduced heat consumption which in turn allows for the application of much higher field strengths. As those skilled in the art will recognize, the high applied field strength result in faster separations improved resolution and sharper detected peak shapes.

In preferred embodiments of the present invention the capillary or electrophoresis channel further incorporates a coating on its inner wall. As known in the art, such coatings on silica based capillaries significantly reduce and in most cases effectively eliminate electroosmotic flow during electrophoresis. Since the electrokinetic migration of charged oligosaccharides occurs in a direction opposite to that of the electroosmotic flow, eliminating this bulk flow avoids unwanted long migration times and poor reproducibility. Capillaries having variety of different coatings are commercially available. Preferred coated capillaries are available from Beckman Instruments and sold under the tradename eCAP.

As described above a variety of detectors and detection techniques are suitable in the practice of the present invention. Those skilled in the art are credited with the ability to carry out the electrophoretic separations using the capillaries and electrophoretic mediums described above. The data obtained following the electrophoretic separation can be used to determine differences in glycosylation between samples. Using standards, the oligosaccharides can be identified and ratios of amount of oligosaccharides at different glycoprotein conjugate sites can be determined.

The present invention may be better understood by reference to the following examples which are intended for purposes of illustration only and should not be construed to limit the scope of the invention.

EXAMPLE 1

Figure 1:
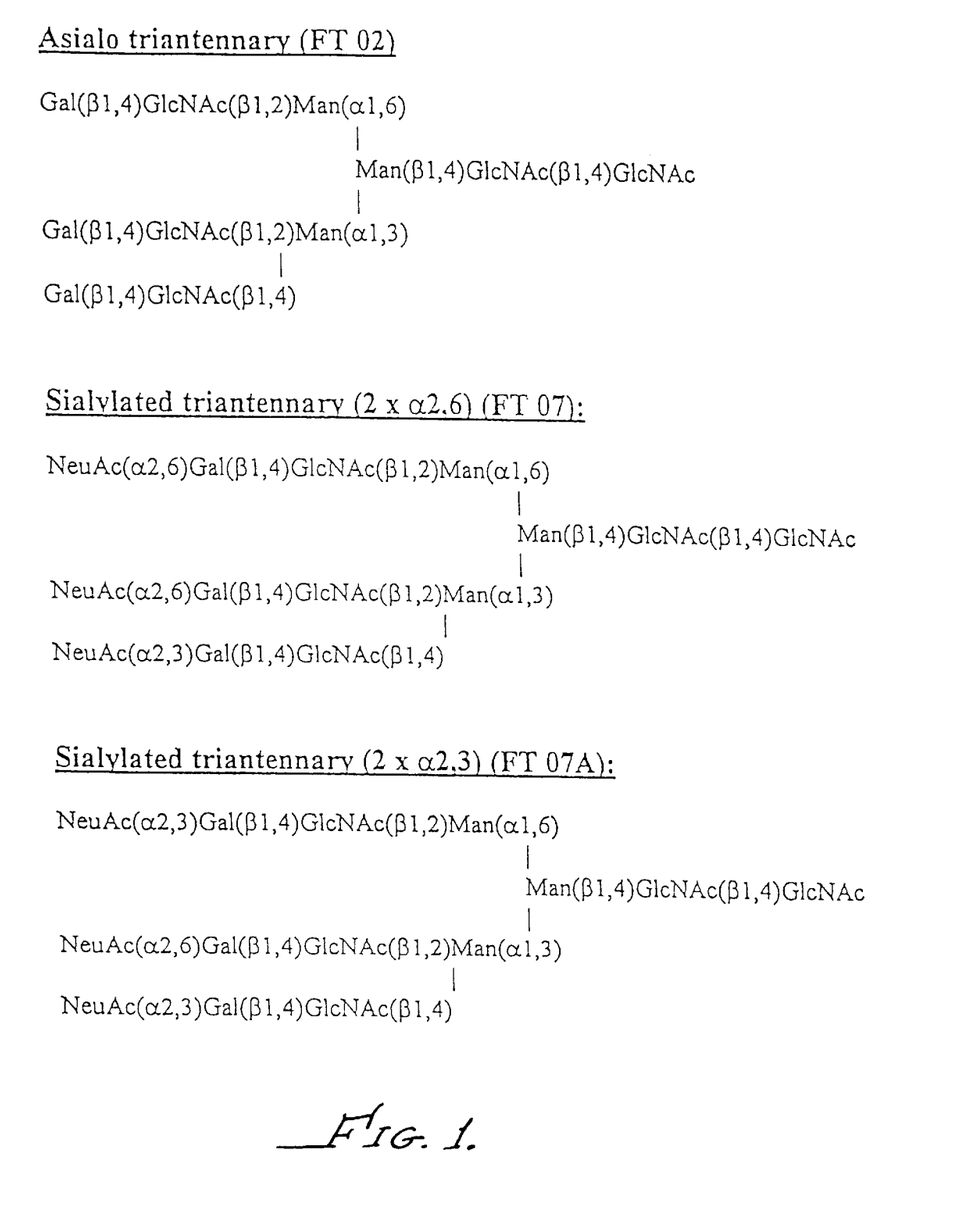
FIG. 1 illustrates the structure of sialylated triantennary oligosaccharide standards utilized to demonstrate the methods of the present invention.

In order to demonstrate the methods of the present invention for its applicability to the analysis of sialylated oligosaccharides and for the purpose of comparing the analysis of sialylated oligosaccharides with a standard ladder of glucose oligomers (maltooligosaccharides), the following experiments were performed. Glucose oligomers were purchased from Grain Processing Co., Muscatine, Iowa. Trisialylated triantennary (2×α2,6) (FT 07), trisialylated triantennary (2×α2,3) (FT 07A) and asialo triantennary (FT 02) glycans were purchased from Dionex (Sunnyvale, Calif.). FIG. 1 illustrates a schematic representation of the structures of these glycans. The oligosaccharides were dried in 0.5 mL microfuge vials with a centrifugal vacuum evaporator. The dried oligosaccharides were then labeled in a reductive amination reaction by the adding 10 $\mu$L of 0.2 M 1-aminopyrene-3,6,8-trisulfonate (APTS) in 15% acetic acid and 10 $\mu$L of 1 M NaBH$_3$CN in tetrahydrofuran to about 1–10 nM of oligosaccharide. The reaction was allowed to proceed for 16 hours at 37° C. and then further diluted in water by 10 times to stop the reaction.

Following the labeling reaction the labeled oligosaccharides were electrophoresed using capillary gel electrophoresis on a P/ACE instrument manufactured by Beckman Instruments. The cathode was on the injection side and the anode on the detection side (i.e., reversed polarity), since the negatively charged labeled oligosaccharide molecules migrate toward the anode under the influence of the electric field. The separations were monitored with a Beckman laser induced fluorescence (LIF) detection system using a 4 mW argon-ion laser with the excitation wavelength of 488 nm and emission wavelength filter of 520 nm. The temperature of the capillary was controlled at 20+/−0.1° C. For the electrophoresis separation, a coated capillary column of 50 $\mu$M i.d. with 50 cm effective length (57 cm total length) was used. The capillary is available from Beckman Instruments and identified as eCAP™ PVA-I type Coated Capillary (described in copending application Ser. No. 08/379,383. The electrophoresis separation medium was a lithium acetate buffer adjusted to a pH of 4.75 and containing a 300,000 MW polyethylene glycol gel. The current resulting from the applied voltage was <20 $\mu$A and the samples were diluted by about 500 times in the acetate buffer prior to injection using the pressure injection mode—typically for 5–10 seconds at 0.5 PSI.

Figure 2:
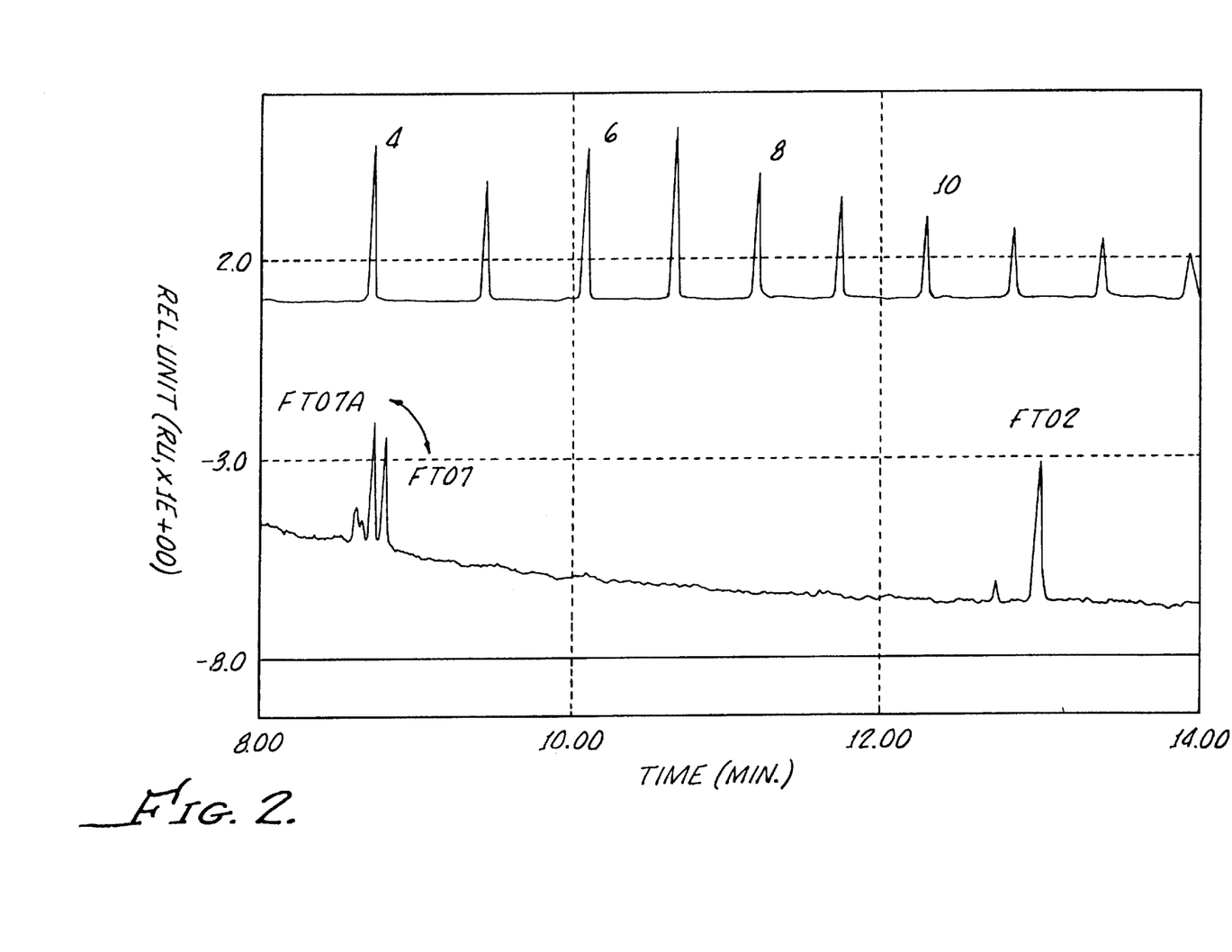
FIG. 2 illustrates electropherograms obtained by electrophoresing labeled maltooligosaccharide ladder standard and three labeled triantennary structures of FIG. 1.

FIG. 2 shows the electropherogram of the labeled maltooligosaccharide ladder standard (the upper trace) and the three APTS labeled triantennary structures: trisialylated triantennary (2×α2,6) (FT 07), trisialylated triantennary (2×α2,3) (FT 07A) and asialo triantennary (FT 02). Two of these glycans differ only by the sialylation linkage (α2,6 vs α2,3) and one of them has no sialylation (the asialo). The lower trace illustrates the separation of the three labeled triantennary compounds. The resulting peak area for the different structures shows only a small variation suggesting a structure and size independence for the labeling and the analysis of these structures by this method.

EXAMPLE 2

The following experiment demonstrates the methods of the present invention for analyzing N-linked oligosaccharides released from the glycoproteins of ribonuclease B and fetuin.

To digest the glycoproteins and release the N-linked oligosaccharides, in separate reactions, 50 $\mu$L of 50 mM phosphate buffer (at pH 7.5) containing 0.1% SDS was added to 50 $\mu$g of each glycoprotein in the presence of 2% 2-mercaptoethanol and heated at 100° C. for 5 minutes. Then 5 $\mu$L of 7.5% NP-40 and 5 mU of recombinant peptide N-glycosidase F, purchased from Glyko, Inc., of Novato, Calif., was added to each reaction mixture and they were incubated for 2 hours at 37° C. The deglycosylated proteins were precipitated by adding 3× volume ice-cold ethanol and then removed by centrifugation at 10,000 rpm. The released oligosaccharides in the supernatant were dried in a centrifugal vacuum evaporator and then labeled with APTS in reductive amination reactions as described in Example 1. In addition to the oligosaccharides released from ribonuclease B and fetuin, a maltooligosaccharide standard ladder mix was derivatized with APTS in the same manner.

Figure 3:
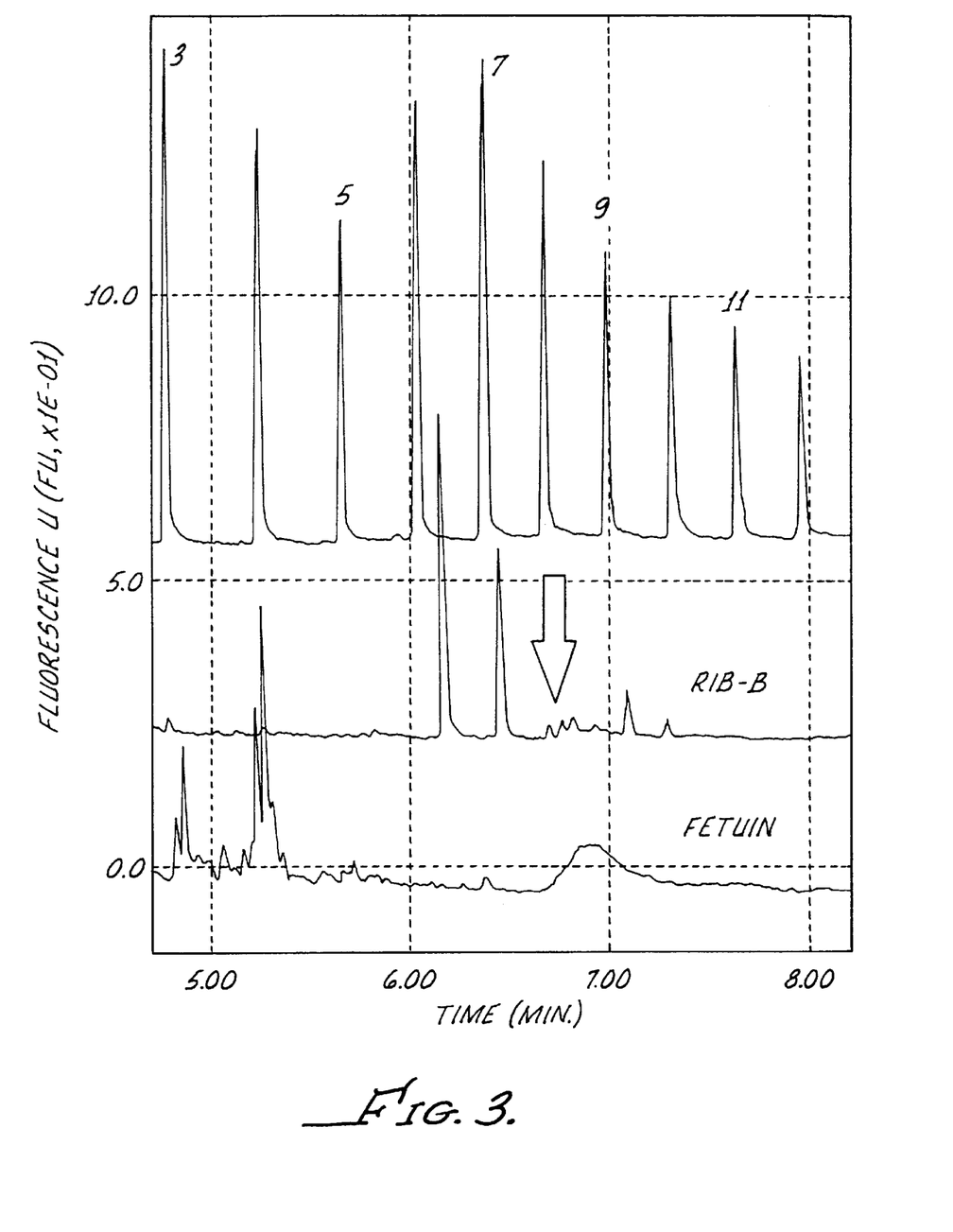
FIG. 3 illustrates electropherograms obtained by electrophoresing asparagine linked oligosaccharides released from ribonuclease B and fetuin compared to a labeled maltooligosaccharide ladder standard.

After diluting each labeled oligosaccharide sample by 500 fold the samples were separately subjected to capillary gel electrophoresis using the same column configuration and separation conditions as described in Example 1. FIG. 3 shows the electropherograms obtained from each of the samples. The APTS labeled maltooligosaccharide ladder standard electropherogram is shown on the upper trace and the APTS labeled ribonuclease B and APTS labeled fetuin electropherograms are shown on the lower traces, respectively. It can be seen that excellent baseline separation of the Man-7 triplet (shown by the arrow) is achieved in the ribonuclease B trace. The identification of the peaks was accomplished by comparing with coinjected purified standards. The degree of glycosylation of ribonuclease B is known to be approximately 10%, and each peak of the Man-7 triplet in the released glycan pool corresponds to ~1% of the total oligosaccharide amount. Based on the above, it can be seen that with no sample dilution before injection, the detected amount would be in the low femtomole range.

The electropherogram obtained from the labeled and released oligosaccharides of fetuin in FIG. 3 exhibits complete separation of two doublets corresponding to the trisialylated triantennary (also proved by coinjection with individual standards) and tetrasialylated triantennary structures (proved by relative migration index calculation).

EXAMPLE 3

In order to demonstrate the effect of different concentrations of polymeric gel additive to the resolution and reproducibility of the separation of labeled linear oligosaccharides and labeled branched oligosaccharides the following experiments were performed.

Figure 4:
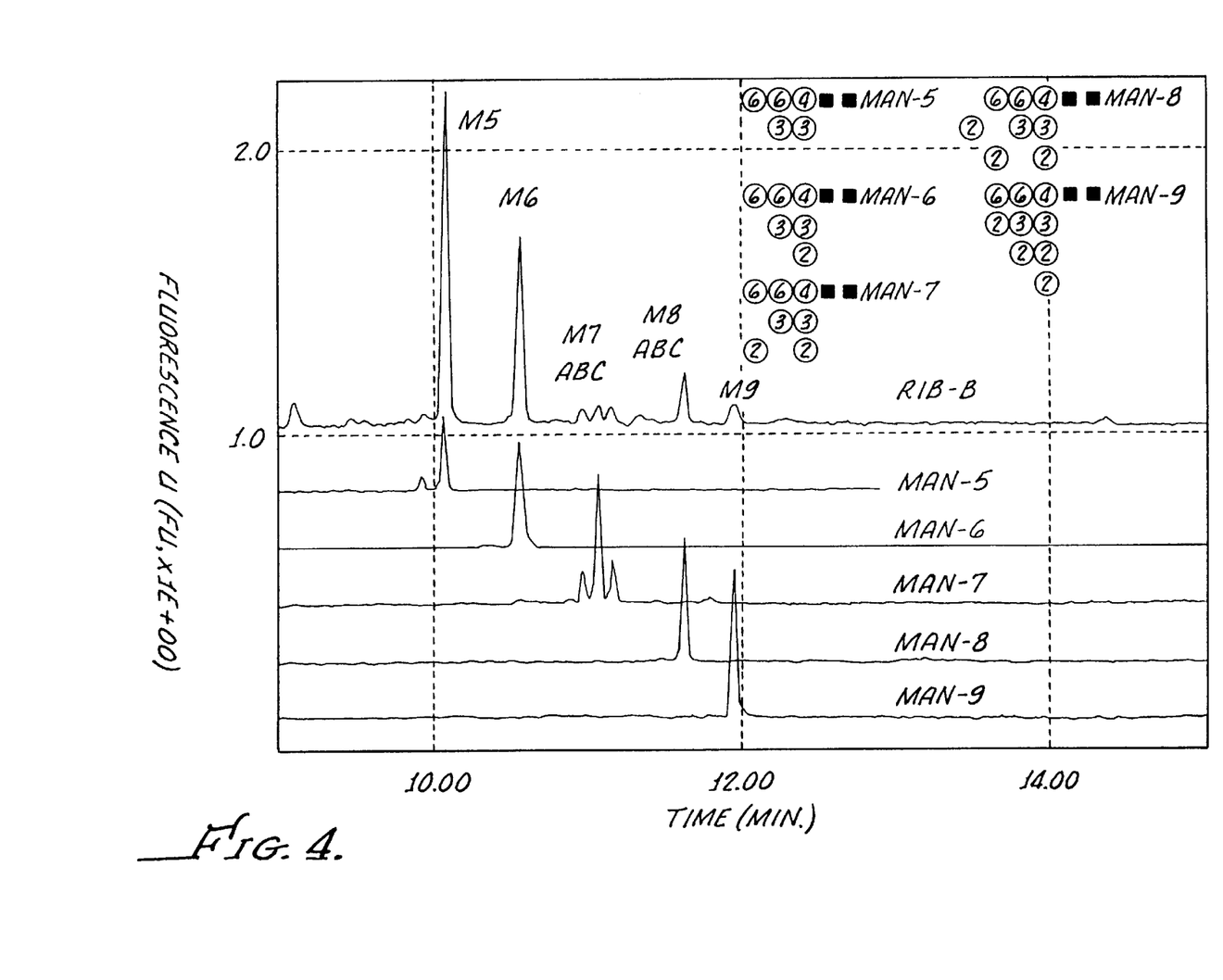
FIG. 4 illustrates electropherograms obtained by electrophoresing asparagine linked oligosaccharides released from ribonuclease B and labeled individual standard oligosaccharides. The electrophoretic separation medium had a pH of 4.75 and an electrophoresis gel.

APTS labeled high-mannose type nitrogen linked oligosaccharides structures released from bovine pancreatic ribonuclease B were prepared in accordance with the digestion and labeling procedures of Examples 1 and 2 above. Additionally, individual standard oligosaccharides of Man-5, Man-6, Man-7, Man-8 and Man-9 were labeled with APTS in the same manner. Electropherograms of the APTS labeled standards and the APTS labeled oligosaccharide samples were obtained in a coated capillary column of 50 μm i.d. and 50 cm effective length (eCAP™ Neutral Coated Capillary from Beckman Instruments). In all the separations, the separation medium and running buffer was a 25 mM lithium acetate buffer adjusted to a pH of 4.75 with phosphoric acid and containing 0.4 wt % polyethylene oxide FIG. 4 illustrates the results of these separations. Identification of the peaks from the ribonuclease B digestion products was accomplished by spiking them with the individual standards (Man-5–Man-9). The upper trace, corresponding to the ribonuclease B released high mannose conjugates, exhibits a nice separation of all the five major and several minor structures. In particular, the baseline separation of the Man-7 and Man-8 triplets has not previously been achieved by HPLC or electrophoresis methods.

FIG. 5 shows electropherograms obtained from the same samples and the commercially available linear part of the core-structure of the high-mannose glycan, Manβ1→4GlcNAcβ1→4Glc NAc (MNN) which were labeled in the same manner as the ribonuclease glycans and the linear glucose oligomers. The electropherograms of FIG. 5 were obtained using the same conditions utilized to obtained the electropherograms of FIG. 4 except that the concentration of polyethylene oxide was varied. In Panel A of FIG. 5 the separations were performed at 0% polyethylene oxide concentration. Panel B–D were obtained with increasing concentrations of polyethylene oxide.

Using the data obtained from the electropherograms, the relative migration index (RMI) described by Stack et al. (Glycobiology, 1992, 2, 85–92) was applied to characterize the relative migration position of the branched high-mannose structures (Man-series) to the linear glucose oligomers (L-series) with identical degree of polymerization (DP) . . . The Man-5 (DP=7) structure migrates with the corresponding degree of polymerization L-7 peak, and the others: Man-6 (DP=8), Man-7 (DP=9), Man-8 (DP=10) and Man-9 (DP=11) also migrate close to their corresponding degree of polymerization ladder components (L-series). However, as the size or the branching of the mannose the structure increases, the higher is their relative mobility, compared to the corresponding DP glucose-ladder

TABLE I

Relative migration indices (RMI) of the high-mannose glycans released from ribonuclease B.

| % PEO | MNN (DP = 3) | Man-5 (DP = 7) | Man-6 (DP = 8) | Man-7 (DP = 9) | Man-8 (DP = 10) | Man-9 (DP = 11) |
|---|---|---|---|---|---|---|
| 0 | 3.31 | 7.08 | 7.9 | 8.98 | 9.87 | 10.56 |
| 0.2 | 3.05 | 6.68 | 7.6 | 8.48 | 9.41 | 10 |
| 0.4 | 2.85 | 6.31 | 7.12 | 8.15 | 9.27 | 9.86 |
| 0.6 | 2.68 | 6.12 | 7 | 7.85 | 8.98 | 9.49 |
| 0.8 | 2.43 | 6 | 6.4 | 7.31 | 7.82 | 7.98 |

Figure 5A:
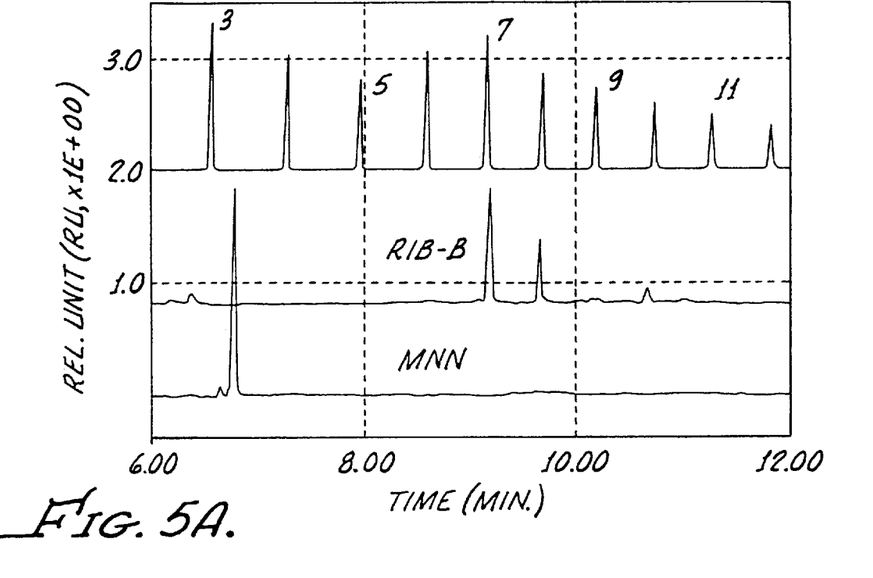
FIGS. 5A–D illustrates electropherograms obtained by electrophoresing asparagine linked oligosaccharides released from ribonuclease B, labeled individual standard oligosaccharides and labeled commercially available high mannose glycans. The electropherograms were obtained using increasing concentrations of electrophoresis gel.
Figure 5B:
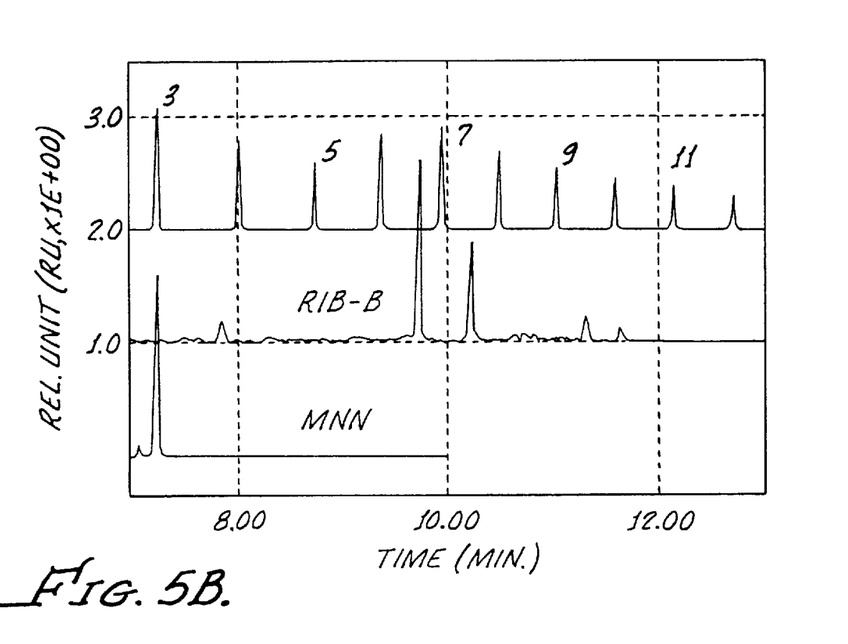
Figure 5C:
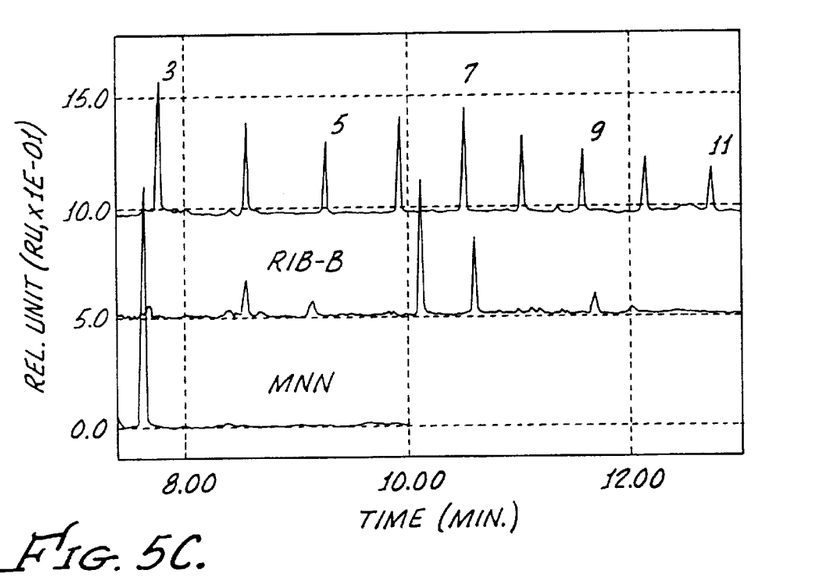
Figure 5D:
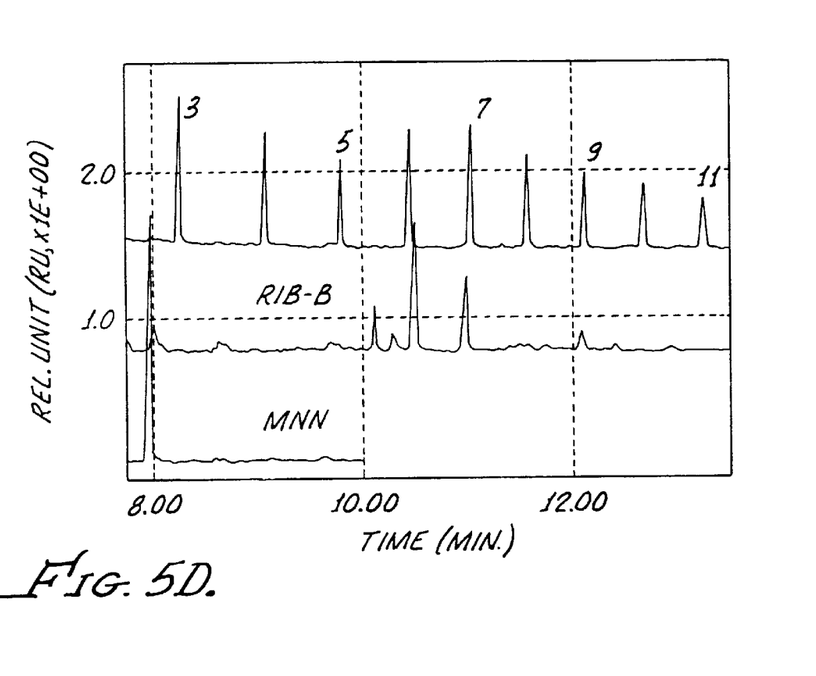

Table I above tabulates the relative migration indices (RMI) of the high mannose glycans released from ribonuclease B. When polyethylene oxide was added to the separation buffer medium in increasing concentrations, the branched high-mannose structures showed increasing relative mobility compared to the linear oligosaccharides as shown in Panels B–D of FIG. 5. Even the linear part of the high-mannose core structure (MNN) shows higher relative mobilities with increasing gel concentration, which suggests that the mannose content in the structures play a role in the change in relative mobility change. It is apparent that the higher the number of mannose units in the glycans, the higher their relative mobility compared to the corresponding DP linear glucose ladders.

Figure 6:
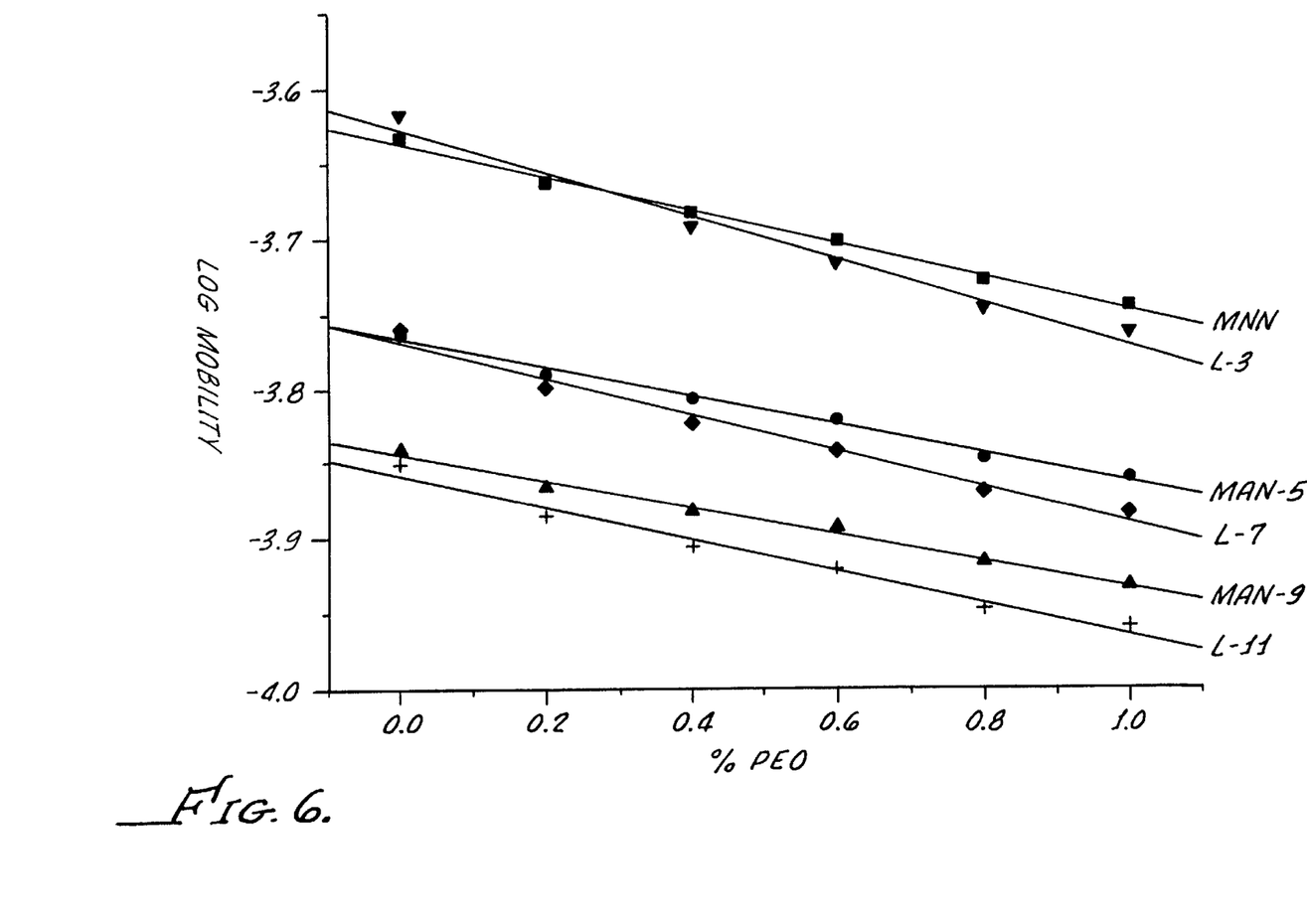
FIG. 6 illustrates Ferguson plots of gel concentration vs. the logarithm of electrophoretic mobility values.

FIG. 6 shows the Ferguson plots of gel concentration vs. the logarithm of electrophoretic mobility values. Corresponding plots of the different oligo-mannose (MNN, Man-5 and Man-9) and linear glucose-oligomer (L-3, L-7 and L-11) structures give similar slopes which suggest no apparent molecular sieving. Therefore, the separation mechanism is based on differences in charge to mass. However, for the similar degree of polymerization structure (MNN vs. L-3, Man-5 vs L-7 and Man-9 vs L-11) the plots in FIG. 6 show different slopes with increasing gel concentrations. These are regular "Ferguson type" convergent lines that cross at different actual and virtual gel concentrations. The MNN and L-3 lines cross at approximately 0.28% polyethylene oxide concentration, causing a peak reversal at higher polymer concentrations. The lines for the Man-5 and L-7 structure cross each other around 0% polyethylene oxide, while the virtual crossing point of the Man-9 and L-11 plots would be in the hypothetical negative region on the gel concentration axis. This effect may be caused by different hydrodynamic radii increments of the oligo-glucose and high-mannose structures or the increased solution viscosity of the different increasing polymer concentrations.

EXAMPLE 4

In the following example the effect of the separation buffer pH on the separation of asparagine linked glycans released from fetuin is demonstrated. The asparagine linked oligosaccharides were released from the glycoprotein fetuin by adding 50 μL, of 50 mM phosphate buffer (pH 7.5) containing 0.1% SDS to 50 μg of lyophilized bovine fetuin and heating at 100° C. for 5 minutes in the presence of 2% 2-mercaptoethanol. Then 5 μL of 7.5% NP-40 and 5 mU of recombinant peptide N-glycosidase (purchased from Glyko) was added to the reaction mixture and the mixture was incubated for 2 hours at 37° C. The deglycosylated proteins were precipitated by the addition of 3× volume ice-cold ethanol and removed by centrifugation at 10,000 rpm. The released oligosaccharides in the supernatant were dried in a centrifugal vacuum evaporator and then labeled in a reductive amination reaction with APTS as described in Example 3. Trisialylated triantennary standard oligosaccharides and maltooligosaccharide ladder standards were labeled with APTS utilizing the same derivatization procedure.

The APTS labeled samples were separated on a Beckman Instruments P/ACE capillary electrophoresis instrument in a neutrally coated capillary column of 50 μm i.d. with 50 cm effective length (eCAP™ PVA-I Coated Capillary). In one set of separations a 25 mM phosphate adjusted to pH 2.5 buffer was utilized in the separation medium and in another set of separations a 25 mM lithium acetate buffer adjusted to a pH of 4.75 was utilized.

Figure 7:
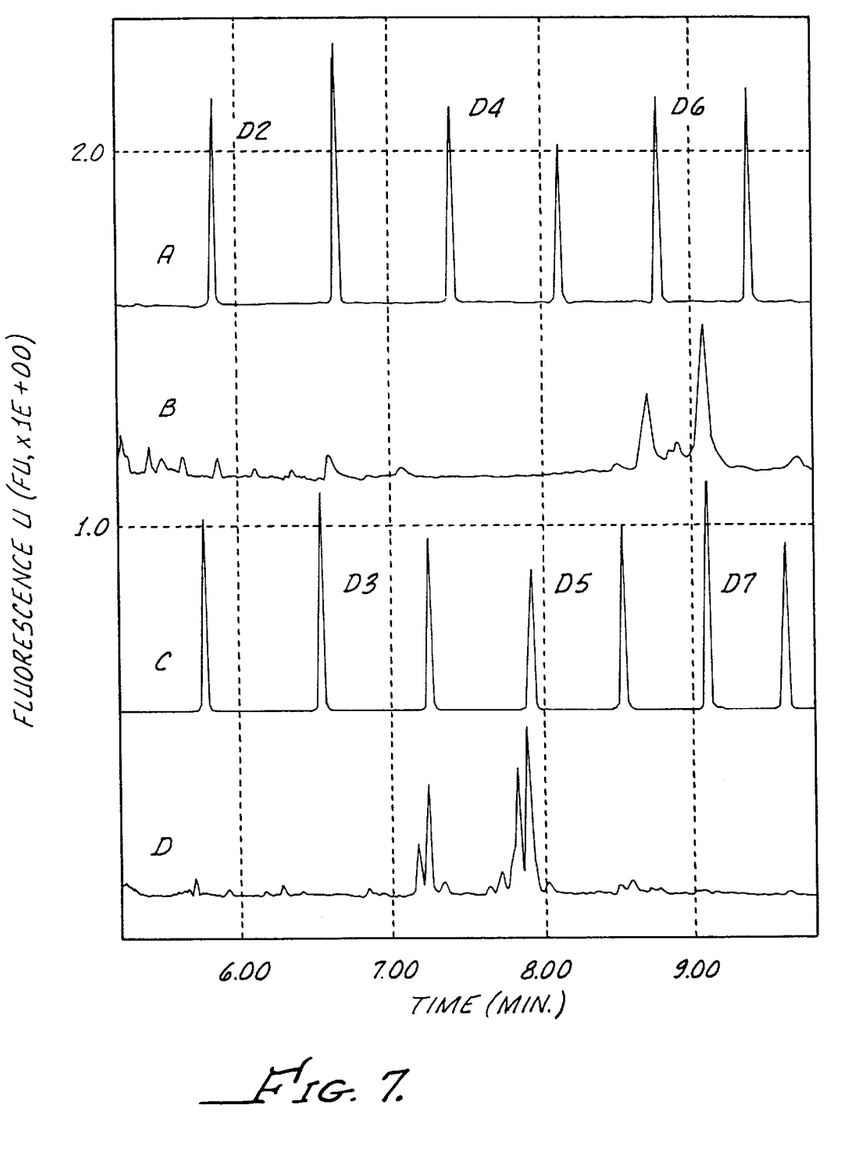
FIGS. 7A–D illustrates electropherograms of labeled maltooligosaccharide ladder and oligosaccharides released from fetuin obtained using pH 2.5 and pH 4.75.

FIG. 7 shows electropherograms of the APTS labeled maltooligosaccharide ladder obtained using pH 2.5 and pH 4.75 (traces A and C, respectively) and electropherograms of the asparagine linked glycans released from fetuin using pH 2.5 and pH 4.75 separation medium (traces B and D, respectively) medium. At pH 2.5, the dissociation of the sialic acid residues on the glycans are depressed. Thus, using this low pH buffer results in longer migration times because the lower charge to mass ratios of the sialylated carbohydrates (trace B in FIG. 7). The two dominate peaks obtained from the labeled oligosaccharides released from the fetuin digestion migrate with mobilities between the maltopentaose (D-5) and maltoheptaose (D-7) peaks of the maltooligosaccharide standard.

When the pH of the separation medium was increased to 4.75, all of the sialic acid are almost completely ionized which causes the same APTS labeled fetuin glycan to migrate faster, under otherwise identical electrophoretic conditions (See trace D). Here the resulting electrophoretic mobilities are similar to that of the maltotetraose (D-4) and maltopentaose (D-5) peaks of the standard glucose ladder (See traces C and D). Another important feature of using pH greater than 2.5 is that the two dominant peaks of trace B are split to four major and several minor peaks, indicating a significantly higher resolving power associated with using the higher pH running buffer.

EXAMPLE 5

The following experiments demonstrate the effect of the absence and presence of gel in the separation medium and provide data demonstrating methods for identifying peaks in glycoprotein profiling methods of the present invention.

Figure 8:
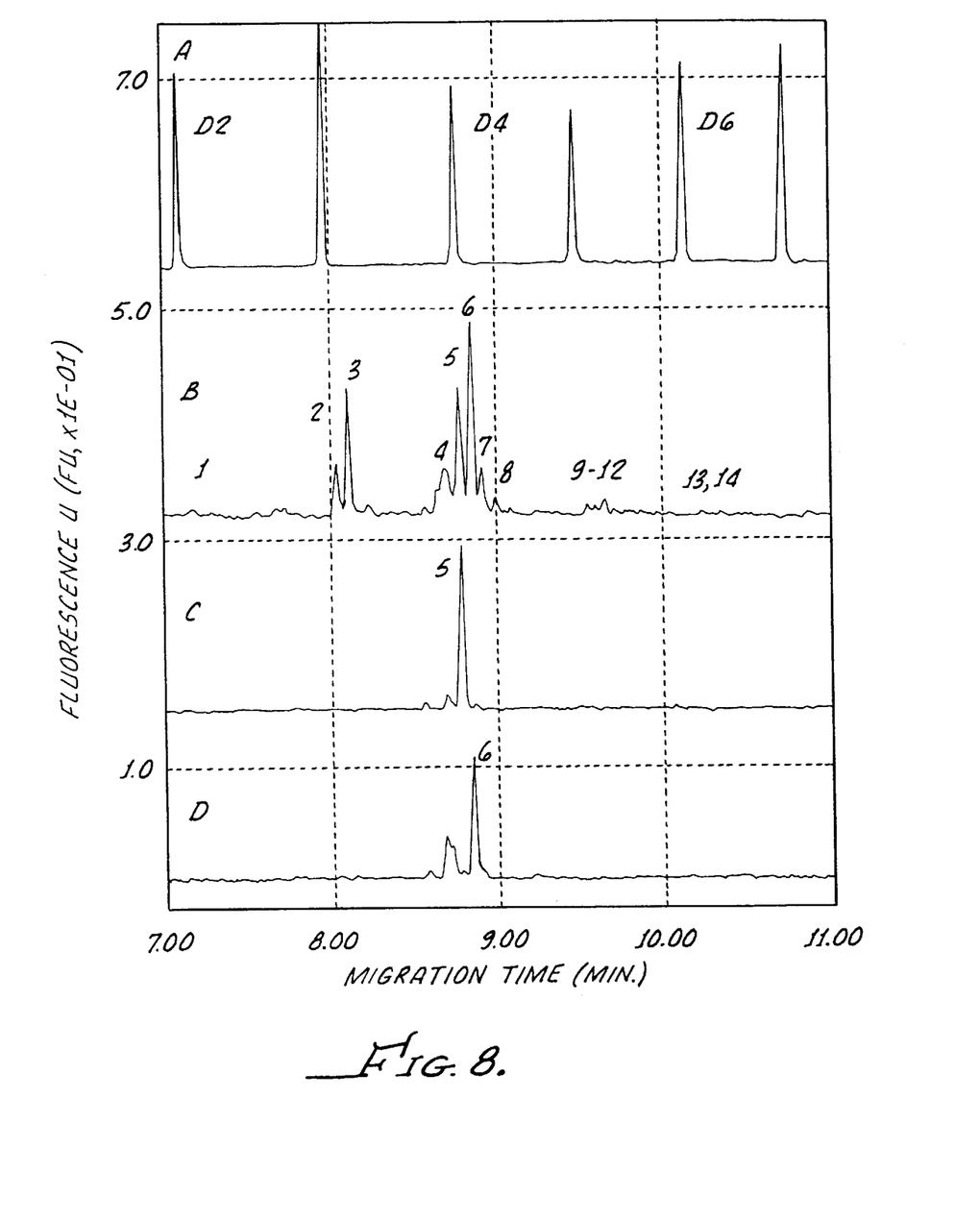
FIGS. 8A–D illustrates electropherogram of FIG. 7 at pH 4.75 using an electrophoresis gel.

The APTS labeled maltooligosaccharide ladder prepared in Example 4, the APTS labeled oligosaccharides released in the fetuin digestion prepared in Example 4, and the APTS labeled trisialylated (2×α2,6)-triantennary and the APTS labeled trisialylated-(2×α2,3)-triantennary standards prepared in Example 1 were electrophoresed using the same electrophoresis conditions described in Example 4 with a pH 4.75 buffer separation medium except that 0.4% polyethylene oxide was added to the pH 4.75 buffer separation medium. FIG. 8 shows the electropherograms obtained from these separations. Trace A is the APTS labeled maltooligosaccharide ladder standard separation; trace B is the APTS labeled fetuin glycan separation; trace C is the APTS labeled trisialylated (2×α2,6)-triantennary standard and trace D is the APTS labeled trisialylated-trisialylated-(2×α2,3)-triantennary standards separation. The results show the addition of 0.4% polyethylene oxide caused a mobility shift of all the sialylated structure, and they comigrate with the linear structure of maltotriose (D-3) and maltotetraose (D-4). Trace B shows an excellent separation of the enzymatically released glycans of the fetuin. Besides the two dominant doublets (peaks 2, 3 and 5, 6), several minor components (peaks 1, 2, 3, 9–14) were separated as well. These results, in combination with the data demonstrated in Example 4, show that the methods of the present invention can be carried out without the addition of a gel to the separation medium. However, the presence of a gel improves the efficiency of the electrophoretic process.

In order to identify peaks associated with the glycans released from fetuin, the labeled trisialylated-(2×α2,6)-triantennary standard and the labeled trisialylated-(2×α2,3)-triantennary standards were coinjected with the labeled glycans released from fetuin. The results of the coinjection study are shown in Table II.

TABLE II

Peaks assigned to Neu5Ac positions and linkages of the triantennary structures of fetuin in CGE

| Peak | 1*,*** | 2** | 3** | 4 | 5 | 6 | 7** | 8** | 9** | 10** | 11** | 12** | 13 | 14 |
|---|---|---|---|---|---|---|---|---|---|---|---|---|---|---|
| GU | 2.1 | 3.1 | 3.2 | 3.9 | 4.0 | 4.1 | 4.2 | 4.3 | 5.4 | 5.5 | 5.5 | 5.6 | 6.4 | 6.5 |
| A | α2,6 | — | — | — | — | — | — | — | — | — | — | — | — | — |
| B | α2,3 | α2,6 | α2,3 | α2,6 | α2,6 | α2,3 | α2,6 | α2,3 | α2,6 | — | α2,6 | α2,3 | α2,6 | α2,3 |
| C | α2,6 | α2,6 | α2,6 | α2,6 | α2,6 | α2,6 | α2,6 | α2,6 | α2,6 | α2,6 | — | — | — | — |
| D | α2,3 | α2,3 | α2,3 | α2,6 | α2,3 | α2,3 | α2,3 | α2,3 | | α2,3 | α2,3 | α2,3 | α2,3 | α2,3 |
| E | α2,6 | α2,6 | α2,6 | — | — | — | — | — | α2,6 | α2,6 | α2,6 | α2,6 | — | — |

```
                              A
                              |
B- Gal(β1,4*)GlcNAc(β1,2)Man(α1,6)
                              |
                              Man(β1,4)GlcNAc(β1,4)GlcNAc
                              |
C- Gal(β1,4)GlcNAc(β1,2)Man(α1,3)
                              |
D- Gal(β1,4**)GlcNAc(β1,4)
                              |
                              E
*Gal(β1,3); **Gal(β1,3)
```

The results suggest that peaks 5 and 6 are trisialylated-(2× α2,6)-triantennary and trisialylated-(2×α2,3)-triantennary structures. These peaks comprise about 67% of the total LIF detector response. Peaks 2 and 3 which are the remaining two major peaks constitute 24% of the LIF response. Since they migrate with a mobility similar to that of the maltotriose peak (GU=3), there is a strong suggestion that they are tetrasialylated-triantennary structures. This is also suggested after comparing the mobilities of peaks 2 and 3 and peaks 5 and 6 with the glucose units (GU) of the maltooligomer ladder). Such a comparison was carried out by calculating the GU values for all structures based on the corresponding glucose unit equivalents of the individual sugars in the possible oligosaccharide structures. The calculations were accomplished by summing the corresponding GU values of the individual contributing sugars for each composition. Table III shows the results of these studies.

TABLE III

Glucose unit (GU) values of different monosaccharides and oligosaccharides in triantannary structures:

| Structures | GU |
|---|---|
| APTS-GlcNAc$_2$Man$_3$ (core) | 4.5 |
| GlcNAc($\beta$1,2/4) | 0.9 |
| Gal($\beta$1,4) | 1.3 |
| Gal($\beta$1,3) | 1.5 |
| Neu5Ac($\alpha$ 2,6) | 2.4 |
| Neu5Ac($\alpha$ 2,3) | 2.3 |
| Neu5Ac($\alpha$ 2,6) linked to GlcNAc($\beta$1,2/4) | 1.1 |

These calculated numbers showed good match to the experimentally obtained values for the trisialylated-(2×α2,6)-triantennary and the trisialylated-(2×α2,3)-triantennary oligosaccharides, i.e. 4.0 and 4.1 for peaks 5 and 6, respectively (See table II).

Using the foregoing approach the structures of peaks 2 and 3, with determined GU units of 3.1 and 3.2, respectively were assigned the suggested tetrasialylated-triantennary structures (See Table II:2 and 3). To assess the structure of other peaks in the electropherograms the same approach was used. If Neu5Ac(α2,6) is connected to terminating Gal(β1, 4), it has a GU value of −2,4, while if the same sialic is connected to the "in-chain" Gal(β1,3) GlcNAc(β1,2/4) it has a GU value of −1,1 (See Table II). The GU values of all the other sugars with different linkages in the triantennary structure including the nitrogen linked core structure of Man$_3$GlcNAc$_2$, are shown in Table III. Thus, peaks 4, 7 and 8 in the group of peaks 4–8, are probably also trisialylated triantennary structures with different α2,3 and α2,6 linkages, having Gal(β1,4)GlcNAC and Gal(β1,3)GlcNAc moieties on the Man(α1,3) side chain. Also based upon GU calculations, the tiny peak with GU~2 (peak 1) could be pentasialylated triantennary oligosaccharide (See Table II:1). The group of sample peaks around GU=5 was assigned the trisialylated triantennary structures with Gal(β1,3) GlcNAc side-chain (See Table II: 9–12). Peaks 13 and 14 were assigned the bisialylated triantennary structures (See Table II: 13 and 14).

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and although specific terms have been employed here, they are intended in a descriptive sense and not for purposes of limitation.

We claim:

1. A process for profiling oligosaccharides released from glycoproteins, said process comprising the steps:

providing an analytical sample comprising said released oligosaccharides;

introducing said sample of released oligosaccharides into an electrophoresis channel, said electrophoresis channel comprising an electrophoretic separation medium having a pH less than 8 and greater than 2.5, wherein said separation medium comprising a lithium acetate buffer;

applying an electric field to said electrophoresis channel sufficient to cause said released oligosaccharides to electrophoretically and differentially migrate within said electrophoresis channel; and detecting said separated oligosaccharides.

2. The process of claim 1 wherein said released oligosaccharides are sialylated.

3. The process of claim 1 wherein said pH is about 4.7.

4. The process of claim 1 wherein said electrophoresis channel is formed by a capillary having a diameter of less than 500 micrometers.

5. The process of claim 1 wherein said electrophoretic separation medium further includes an electrophoresis gel.

6. The process of claim 5 wherein said electrophoresis gel includes between 0.01 and 1.0% polyethylene oxide.

7. The process of claim 1 wherein said released oligosaccharides incorporate a detectable label.

8. The process of claim 7 wherein said detectable label is selected from the group consisting of ultra-violet chromophores, visible chromophores, and fluorescent chromophores.

9. A process for profiling oligosaccharides conjugated to glycoproteins, said process comprising the steps:

releasing released oligosaccharides from said glycoproteins;

introducing a sample of said released oligosaccharides into a capillary, said capillary comprising an electrophoretic separation medium having a pH less than 8 and greater than 2.5, wherein said separation medium comprising a lithium acetate buffer;

applying an electric field to said capillary sufficient to cause said released oligosaccharides to electrophoretically and differentially migrate within said electrophoresis channel; and detecting said separated oligosaccharides.

10. The process of claim 9 further including the step of labeling said released oligosaccharide with a fluorescent label.

11. The process of claim 10 wherein said fluorescent label is 1-aminopyrene-3,6,8-trisulfonate.

12. The process of claim 9 wherein said separation medium comprises an electrophoresis gel.

13. The process of claim 12 wherein said electrophoresis gel includes about 0.4% polyethylene oxide.

14. The process of claim 12 wherein said lithium acetate buffer is present at a concentration of 25 mM and the electrophoresis gel is 0.4% polyethylene oxide.

15. The process of claim 9 wherein detecting said separated oligosaccharides is accomplished with a laser induced fluorescence detector.

16. The process of claim 9, wherein said pH is about 4.7.

* * * * *